(12) United States Patent
Dixon et al.

(10) Patent No.: US 9,044,009 B2
(45) Date of Patent: Jun. 2, 2015

(54) USE OF EDDS AND CALCIUM IONS AS ENHANCERS OF MOLLUSCICIDAL ACTIVITY

(75) Inventors: Nicholas John Dixon, Chester Cheshire (GB); Derek Bassett, Chester Cheshire (GB); Reinhard Arndt, Emmerthal (DE); Andreas Prokop, Halle (DE); Diana Parker, Brentwood Bay (CA); Tianye Chen, Victoria (CA)

(73) Assignee: W.NEUDORFF GMBH KG, Emmerthal (DE)

( * ) Notice: Subject to any disclaimer, the term of this patent is extended or adjusted under 35 U.S.C. 154(b) by 134 days.

(21) Appl. No.: 13/146,098

(22) PCT Filed: Jan. 26, 2010

(86) PCT No.: PCT/GB2010/050114
§ 371 (c)(1),
(2), (4) Date: Oct. 5, 2011

(87) PCT Pub. No.: WO2010/084361
PCT Pub. Date: Jul. 29, 2010

(65) Prior Publication Data
US 2012/0027832 A1 Feb. 2, 2012

(30) Foreign Application Priority Data

Jan. 26, 2009 (GB) .................................. 0901234.5
Jan. 26, 2009 (GB) .................................. 0901293.1

(51) Int. Cl.
*A01N 25/00* (2006.01)
*A01N 59/26* (2006.01)
*C05G 3/02* (2006.01)

(52) U.S. Cl.
CPC ............ *A01N 25/008* (2013.01); *A61K 35/618* (2013.01); *A01N 59/26* (2013.01); *C05G 3/02* (2013.01)

(58) Field of Classification Search
CPC .................................................. A61K 35/618
See application file for complete search history.

(56) References Cited

U.S. PATENT DOCUMENTS

| 5,437,870 | A | 8/1995 | Puritch et al. |
| 6,258,750 | B1 | 7/2001 | Simpson et al. |
| 6,271,177 | B1 | 8/2001 | Hudetz et al. |
| 6,323,153 | B1 | 11/2001 | Smiley |
| 6,352,706 | B1 | 3/2002 | Puritch et al. |
| 6,972,273 | B2 | 12/2005 | Sedun et al. |
| 2007/0148203 | A1* | 6/2007 | Parker et al. ............. 424/410 |
| 2010/0183533 | A1* | 7/2010 | Giles et al. ............... 424/62 |

FOREIGN PATENT DOCUMENTS

| AU | 77420/98 A | 9/1998 | |
| GB | 2 207 866 A | 2/1989 | |
| WO | WO99/39576 | 8/1999 | |
| WO | WO 9939576 A1 * | 8/1999 | ............ A01N 25/00 |
| WO | 0150862 A1 | 7/2001 | |

OTHER PUBLICATIONS

Alkaline earth metal (http://en.wikipedia.org/wiki/Alkaline_earth_metal (downloaded on Feb. 13, 2013)).*
Horsak et al, Plant indicator values as a tool for land mollusc autecology assessment, Acta Oecologica, 2007, vol. 32, pp. 161-171.*
International Search Report and Written Opinion mailed Mar. 1, 2011 for Application No. PCT/GB2010/050114 (11 Pages).
International Preliminary Report on Patentability mailed Jul. 12, 2011 for Application No. PCT/GB2010/050114 (15 Pages).
Henderson et al., Problems in developing chemical control of slugs. Aspects of Applied Biology. 1986;13:341-347.
Henderson et al., Control of slugs with contact-action molluscicides. Annals of Applied Biology. Apr. 1990;116 (2):273-278.

* cited by examiner

*Primary Examiner* — Paul Dickinson
(74) *Attorney, Agent, or Firm* — Mintz Levin Cohn Ferris Glovsky and Popeo, P.C.

(57) ABSTRACT

A molluscicidal composition, comprising: a molluscicide; a molluscicidal activity promoting additive comprising a calcium-containing salt of ethylene disuccinic acid or calcium ions and ethylenediamine disuccinic moieties, having at least 1 mole of calcium per mole of ethylenediamine disuccinic acid; and a carrier material edible to molluscs.

54 Claims, No Drawings

USE OF EDDS AND CALCIUM IONS AS ENHANCERS OF MOLLUSCICIDAL ACTIVITY

CROSS REFERENCE TO RELATED APPLICATIONS

The present application claims the benefit of priority to PCT/GB2010/050114 filed Jan. 26, 2010 and entitled "USE OF EDDS AND CALCIUM IONS AS ENHANCERS OF MOLLUSCICIDAL ACTIVITY," which claims priority to GB 0901234.5 filed on Jan. 26, 2009 and GB 0901293.1 filed on Jan. 26, 2009. These references are hereby incorporated by reference in their entireties.

FIELD OF THE INVENTION

This invention relates to pest control compounds and, more particularly, to compositions effective to control pest molluscs by enhancing the efficacy of molluscicidal compounds by improving one or more of their palatability, digestion, absorption and residual effects.

BACKGROUND OF THE INVENTION

Terrestrial pulmonate gastropods such as slugs and snails are significant plant pests that affect commercial agriculture and horticulture and domestic gardens. These organisms are omnivorous and consume large amounts of vegetative material during their daily foraging. Consequently, they can seriously damage vegetable gardens and even plant crops during all phases of the growing cycle. Because of their destructive potential, control measures must be used to ensure adequate protection of the growing plants.

Aquatic molluscs, including the fresh water snails, Golden Apple Snail, *Pomacea canaliculata, Bulinsu* sp., *Bulinus, Biomphalaria*, and *Oncomeania*, and vectors of parasitic worms (e.g., *Schistosoma*), are also pests. Aquatic molluscs are controlled by a number of synthetic and botanical compounds. Terrestrial pulmonate gastropods and aquatic molluscs are collectively referred to herein as "molluscs".

A wide variety of approaches have been used to combat pest molluscs. Perhaps the most common is the use of poisonous compounds called molluscicides. Molluscicides encompass a diverse group of chemical compounds including table salt (NaCl), calcium arsenate, copper sulfate and metaldehyde. Molluscicides, depending upon their mode of action, fall into two major groups: (1) contact poisons or (2) ingested poisons. As a contact poison, the molluscicides must come into physical contact with the exterior of the mollusc, either by external application or as a result of the mollusc traversing the bait on the ground. The poison is picked up by the proteinaceous slime coat of the mollusc and builds up in the mollusc's body until it reaches lethal proportions. One of the major drawbacks of contact-type molluscicides is that they have little effect if the molluscs are not physically touched by the chemical. Slugs or snails will be unaffected if they are hidden or migrate into an area after application of a contact molluscicide.

One of the few compounds that acts as both a contact and ingested poison is metaldehyde. This compound is commonly used as a long lasting bait, attracting the molluscs and killing them after ingestion of the compound. Despite its high effectiveness and its commercial popularity, metaldehyde is toxic to higher mammals and is a major contributor to domestic animal poisoning in the U.S. and Europe.

Heavy metals, including zinc, aluminum, copper and iron are all toxic to molluscs and are known to be effective molluscicides when used as contact poisons in the form of salts or chelates (Henderson, et al. 1990). Few of them, however, have been successful commercially, perhaps because many such compounds are not palatable to molluscs and are not ingested in sufficient quantities to be effective. Henderson et al. (UK Patent Application 2 207 866A, 1988) discovered that specific complexes of aluminum with pentanedione compounds and iron with nitroso compounds would act both as ingested and contact poisons.

U.S. Pat. No. 5,437,870 (Puritch et al) discloses an ingestible mollusc poison having a carrier (e.g., a bait), a simple iron compound and a second component. The second component can be ethylene diamine tetracetic acid (EDTA), salts of EDTA, hydroxyethlene triamine diacetic acid, (HEDTA) or salts of HEDTA. Australian Patent Application No. 77420/98 also discloses a stomach-action molluscicide that includes a metal complexone (i.e., iron EDTA) and a carrier. U.S. Pat. No. 6,352,706, discloses the composition and use of an activity promoting additive, ethylene diamine disuccinic acid (EDDS) and derivatives thereof in combination with an edible carrier.

U.S. Pat. No. 6,352,706, mentioned above, discloses that metal, especially iron molluscicidal baits, could be improved by the additive EDDS which enhanced the effectiveness of metal absorption in molluscs.

With the ingested poisons, the slug must eat and absorb the poison in large enough amounts to reach a lethal threshold. These baits are much more difficult to formulate and use than are contact poisons because the compounds are not always palatable to the slug. To be effective, these compounds must be formulated in baits that are readily eaten by the molluscs in sufficient quantities to cause a poisoning effect. If bait is too poisonous, the molluscs will cease feeding prior to absorbing enough toxins to be lethal. On the other hand, if the bait is not toxic enough the molluscs will simply eat and excrete the bait without being affected (Henderson and Parker, 1986).

It would thus be desirable to provide a molluscicidal bait composition that will enhance palatability, ingestion, digestion and residual action of stomach-action molluscicides.

WO 99/39576 describes a mollusc stomach poison composition that comprises a simple metal compound, an additive that enhances the activity and absorption of the metal, and a carrier material that is edible to molluscs. The composition is effective to combat molluscs upon being ingested by the molluscs.

According to WO 99/39576, useful salts of ethylene diamine disuccinic acid that may serve as an activity enhancing additive according to the present invention include alkali metal salts, alkali earth salts, ammonium salts and substituted ammonium salts of this compound, as well as mixtures thereof. Preferred salts include the sodium, potassium, and ammonium salts. The use of pH-adjusting additives is described in WO 99/39576, including calcium carbonate, potassium carbonate, potassium hydroxide, ascorbic acid, tartaric acid and citric acid.

Slug pellets made according WO 99/39576 are very effective but there is always a need for new and/or improved compositions.

SUMMARY OF THE INVENTION

In accordance with a first aspect the invention provides a molluscicidal composition, comprising:

a molluscicidal activity promoting additive comprising calcium ions and ethylenediamine disuccinic moieties; and a carrier material edible to molluscs.

The composition is intended to be effective to combat molluscs upon being ingested by the molluscs.

The use of the defined molluscicidal activity promoting additive is believed to lead to a good level of ingestion of the composition, and to enhance digestion of a molluscicide. It is believed that its use may lead to a molluscicide of extended duration.

By "combat" herein we mean it may repel, deter, injure, disable or, preferably, kill molluscs.

The composition is suitably effective to combat, preferably kill, molluscs upon being ingested by the molluscs. The composition can be used alone or with other components or compositions, e.g. molluscicides, to enhance the palatability of the other composition, and the likelihood that the molluscs will ingest the composition.

The baits may contain a metal compound which may be a simple metal compound, preferably selected from the group consisting of iron, copper, zinc, aluminum, and mixtures thereof. The term "iron" as used herein is understood to refer to both the ferric and ferrous forms of iron. The palatability and digestion (or absorption) enhancing additive is $Ca_2EDDS$. The carrier material is one that is edible to molluscs, and it preferably is a mollusc food.

In another embodiment the molluscicidal baits may also include a molluscicide or other co-active ingredient, such as metaldehyde, iron phosphate, iron chelate such as iron EDTA or iron HEDTA or iron polyphosphonate. In yet another embodiment the composition may include or be used with a fertilizer compound, such as a granular fertilizer.

As used herein, the term "mollusc" refers to both terrestrial and aquatic molluscs.

DETAILED DESCRIPTION OF THE INVENTION

The present invention provides a composition that is an improved ingestible mollusc bait. In one embodiment, the composition includes the activity promoting additive, $Ca_2EDDS$, which is believed to increase the ingestion, digestion and residual action of the molluscicidal baits. In another embodiment the baits may contain a simple metal compound and/or chelators. Additional formulation enhancing additives may be included as well. Examples of such compounds include pH-adjusting compounds, preservatives, anti-microbial agents, phagostimulants, and taste-altering additives.

The metal compound can be one that includes metals such as iron, copper, zinc, aluminum or mixtures thereof. Such a compound may be reduced elemental iron, metal proteins (e.g., iron proteins, copper proteins, zinc proteins, aluminum proteins), metal salts (e.g., iron salts, copper salts, zinc salts, aluminum salts and mixtures thereof), metal carbohydrates (e.g., iron carbohydrates, copper carbohydrates, zinc carbohydrates, aluminum carbohydrates and mixtures thereof). Specific examples of such compounds include iron acetate, iron chloride, iron phosphate, iron phosphate/sodium citrate mixture, sodium iron phosphate, iron pyrophosphate, iron nitrate, iron ammonium sulfate, iron albuminate, iron sulfate, iron sulfide, iron choline citrate, iron glycerol phosphate, iron citrate, iron ammonium citrate, iron fumarate, iron gluconate, iron lactate, iron saccharate, iron fructate, iron dextrate, iron succinate, iron tartrate, copper acetate, copper chloride, copper phosphate, copper pyrophosphate, copper nitrate, copper ammonium sulfate, copper albuminate, copper sulfate, copper gluconate, copper lactate, copper saccharate, copper fructate, copper dextrate, zinc acetate, zinc chloride, zinc phosphate, zinc pyrophosphate, zinc nitrate, zinc ammonium sulfate, zinc albuminate, zinc sulfate, zinc gluconate, zinc lactate, zinc saccharate, zinc fructate, zinc dextrate, aluminum acetate, aluminum chloride, aluminum phosphate, aluminum pyrophosphate, aluminum nitrate, aluminum ammonium sulfate, aluminum albuminate, aluminum sulfate, aluminum gluconate, aluminum lactate, aluminum saccharate, aluminum fructate, and aluminum dextrate. It is understood that the term "iron" as used herein refers to both the ferric and ferrous forms of this element.

As noted above, the activity promoting additive is one that improves the ingestion, digestion and residual action of molluscicidal baits, and especially the efficacy of baits directly applied to water for the control of aquatic snails. In one embodiment the activity promoting additive is $Ca_2EDDS$.

Ethylenediamine disuccinic acid has the structure shown below:

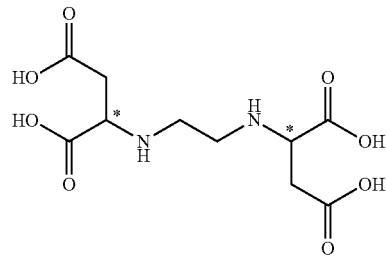 [SMILES: O=C(O)CC(NCCNC(CC(=O)O)C(=O)O)C(=O)O]

The structure includes two stereogenic centres and three possible stereoisomers exist. An especially preferred configuration is S,S ethylenediamine disuccinic acid as this compound is readily biodegradable.

Compositions comprising ethylenediamine disuccinic acid and sodium salts thereof are very widely used particularly as chelating agents.

In this specification, the abbreviation "EDDS" is used to denote the structure shown above and said structure in which a number of the hydroxyl hydrogen atoms have been replaced i.e., "EDDS" may also be used to refer to succinate salts in which 1, 2, 3 or 4 of the acid groups have been neutralised or partially neutralised. Derivatives of EDDS maintaining the ethylenediamine disuccinic skeleton or structure—for example functionalised EDDS-based compounds—are included in the scope of the invention.

One commercially available material is trisodium ethylenediamine disuccinate. It can be purchased as an aqueous solution comprising 30 wt % EDDS (expressed as free acid) or 37 wt % of trisodium EDDS (including the counterion).

Ethylenediamine disuccinic acid is also commercially available in the form of a solid powder, which contains 65 wt % solid [S,S] EDDS as an acid, and water of crystallisation.

In a preferred molluscicidal composition of the first aspect the activity promoting additive has at least 0.1 mole of calcium ions per mole of ethylenediamine disuccinic acid, preferably at least 0.2, preferably at least 0.3, preferably at least 0.4, preferably at least 0.5, preferably at least 0.6, preferably at least 0.7, preferably at least 0.8, preferably at least 0.9, preferably at least 1, preferably at least 1.1, preferably at least 1.2, preferably at least 1.3, preferably at least 1.4, preferably at least 1.5, preferably at least 1.6, preferably at least 1.7, preferably at least 1.8, preferably at least 1.9, moles of calcium ions per mole of ethylenediamine disuccinic moieties.

In the case of salts of calcium ions and EDDS anions there is preferably at least 1 mole of calcium ions per mole of ethylenediamine disuccinic acid, preferably at least 1.1, preferably at least 1.2, preferably at least 1.3, preferably at least 1.4, preferably at least 1.5, preferably at least 1.6, preferably at least 1.7, preferably at least 1.8, preferably at least 1.9, moles of calcium ions per mole of ethylenediamine disuccinic moieties.

The presence of ions other than calcium in the activity promoting additive is not excluded. Such further ion species may include alkali metal ions, for example sodium or potassium and other alkaline earth metal ions, for example magnesium.

In a preferred molluscicidal composition of the first aspect calcium ions are the only alkaline earth metal ions in the activity promoting additive.

In a preferred molluscicidal composition of the first aspect calcium ions are the only metal ions in the activity promoting additive.

In a preferred embodiment the activity promoting additive comprises a calcium-containing salt of ethylenediamine disuccinic acid.

Preferably calcium is the only alkaline earth metal ion in the calcium-containing salt.

Preferably calcium is the only metal ion in the calcium-containing salt.

In a preferred embodiment the activity promoting additive comprises the dicalcium salt of ethylenediamine disuccinic acid.

In a preferred embodiment of the molluscicidal composition of composition of the first aspect the activity promoting additive comprises an admixture, preferably formed in the solid phase, of a calcium compound and ethylenediamine disuccinic moieties. Suitably the activity promoting compound may comprise an admixture, preferably formed in the solid phase, of a calcium compound and ethylenediamine disuccinic acid.

Specific examples of calcium compounds include calcium hydroxide, calcium carbonate, calcium oxide, calcium bicarbonate, calcium acetate, calcium chloride, calcium phosphate, calcium phosphate/sodium citrate mixture, sodium calcium phosphate, calcium pyrophosphate, calcium nitrate, calcium albuminate, calcium sulphate, calcium sulphide, calcium choline citrate, calcium glycerol phosphate, calcium citrate, calcium fumarate, calcium gluconate, calcium lactate, calcium saccharate, calcium fructate, calcium dextrate, calcium succinate and calcium tartrate.

Preferably the calcium compound is selected from calcium hydroxide and calcium carbonate.

A reaction between a simple calcium salt and ethylenediamine disuccinic moieties to form a salt is preferably carried out in the liquid phase, preferably in a solvent, for example water. For this purpose any of the above calcium salts which are sufficiently soluble in the solvent may be used.

Admixture of a calcium salt and ethylenediamine disuccinic moieties is preferably carried out in the solid phase prior to introduction to the molluscicide and other components of the composition, and the calcium salt and the compound which is the source of the EDDS anions are mixed together in a comminuted form (for example as powder or granules). Any calcium salt which has a blendable solid form at ambient temperature of 20° C. may be employed. Any source of EDDS anions which has a suitable solid form at ambient temperature of 20° C. may be employed. Suitable, and preferred, is ethylenediamine disuccinic acid.

Preferably the activity promoting additive comprises at least 50% [S,S]-EDDS, preferably at least 70%, more preferably at least 90%. In some preferred embodiments the salt consists essentially of an alkaline earth metal salt of [S,S]-EDDS.

A preferred activity promoting additive $Ca_2EDDS$ is believed to attract molluscs because of their need to obtain calcium from the environment. In the chelated form, $Ca_2EDDS$ is highly soluble and readily absorbed and metabolized by the molluscs. It is believed that molluscicidal compositions having calcium cations and EDDS anions are more readily sought out by the molluscs, are ingested in greater amounts and at a faster rate, and are effective over a longer period of time.

The quick ingestion and/or digestion of the poisonous metal compounds results in rapid, irreversible destruction of the cellular integrity of the mollusc, which prevents the molluscs' continued feeding on plant material, eventually leading to death.

Suitable carrier materials are those that are edible to molluscs. Mollusc foods are an example of a preferred type of carrier material. Examples of suitable mollusc food carriers include wheat flour, wheat cereal, meadowfoam, agar, gelatin, oil cake, pet food wheat, soya, oats, corn, citrus mash, rice, fruits, fish by-products, sugars, coated vegetable seeds, coated cereal seeds, casein, blood meal, bone meal, yeast, fats, beer products, and mixtures thereof. Examples of particularly useful mollusc foods include a bone meal—wheat flour mixture having a ratio of bone meal to wheat flour in the range of 50:50 to 90:10 and one formed from wheat flour and sugar at a ratio of wheat flour to sugar in the range of about 90:10 to 95:5.

Other compounds, as noted above, may be added to the composition as formulation enhancing additives. Such compounds include further chelating agents, preservatives or antimicrobial agents, phagostimulants, waterproofing agents, taste altering additives, and pH-adjusting additives.

Suitable chelating agents include, for example, aconitic acid, alanine diacetic acid (ADA), alkoyl ethylene diamine triacetic acids (e.g., lauroyl ethylene diamine triacetic acids (LED3A)), aminotri(methylene-phosphonic acid) (ATMP), asparticaciddiacetic acid (ASDA), asparticacidmonoacetic acid, diamino cyclohexane tetraacetic acid (CDTA), citraconic acid, citric acid, 1,2-diaminopropanetetraacetic acid (DPTA-OH), 1,3-diamino-2-propanoltetraacetic acid (DTPA), diethanolamine, diethanol glycine (DEG), diethylenetriaminepentaacetic acid (DTPA), diglycolic acid, dipicolinic acid (DPA), ethanolaminediacetic acid, ethanoldiglycine (EDG), ethionine, ethylenediamine (EDA), ethylenediamine-diglutaric acid (EDDG), ethylenediaminedi(hydroxyphenyl-acetic acid (EDDHA), ethylenediamine-dipropionic acid (EDDP), ethylenediaminedisuccinate (EDDS), ethylene-diaminemonosuccinic acid (EDMS), ethylenediaminetetra-acetic acid (EDTA), ethylene-bis(oxyethylenenitrilo)tetraacetic acid (EGTA), gallic acid, glucoheptonic acid, glutamicaciddiacetic acid (GLDA), glutaric acid, gluconic acid, glyceryliminodiacetic acid, glycinamidedisuccinic acid (GADS), glycoletherdiamine-tetraacetic acid (GEDTA), 2-hydroxyethyldiacetic acid, hydroxyethylenediaminetri-acetic acid (HEDTA), hydroxylethyldiphosphonic acid (HEDP), hydroxyiminodiacetic acid (HIDA), iminodiacetic acid (IDA), iminodisuccinic acid (IDS), hydroxyimino-disuccinic acid (HIDS), itaconic acid, lauroyl ethylene diamine triacetic acids (LED3A), methylglycinediacetate (MGDA), methyliminodiacetic acid (MIDA), monoethanolamine, nitnilotriacetic acid (NTA), nitrilotripropionic acid (NPA), saccharates, salicylic acid, serine-diacetic acid (SDA), sorbic acid, succinic acid, tartaric acid, tartronic acid, triethanolamine, triethylenetetraamine, and combinations thereof. Preferably, the chelating agent is an aminopolycarboxylic acid, an amine, an amide, a carboxylic acid, a phosphonic acid and combinations thereof. More preferably, the chelating agent is EDTA, HEDTA, HEDP, DTPA and combinations thereof. Other suitable chelating agents capable of complexing metal ions include, for example, amino acids, such as aspartic acid, glutamic acid, and lysine, as well as proteins, such as whey powder, casein, and albumen. Derivatives of the said chelating agents maintaining their skeleton or structure—for example functionalised compounds—are included in the scope of the definitions.

Exemplary preservatives include Legend MK®, available from Rohm & Hass Company of Philadelphia, Pa., and CA-24, available from Dr. Lehmann and Co. of Memmingen/Allgäu, Germany. Preservatives such as these can normally be mixed with water to form a stock solution to be added to the formulation at a concentration in the range of about 10-750 ppm.

Phagostimulants can be added to the composition to attract molluscs and to induce molluscs to feed upon the composition. A variety of phagostimulants can be used, including sugars, yeast products, and casein. Sugars, such as sucrose, are among the more preferred phagostimulants. These additives are normally incorporated within the composition in a dry form. Typically, they can be added to the composition at about 1 to 2.5% by weight of the total composition.

Waterproofing agents, which can also act as binders, can be added to the composition to improve the weatherability of the composition. These are typically water insoluble compounds such as waxy materials and other hydrocarbons. Examples of suitable waterproofing agents are paraffin wax, stearate salts, beeswax, and similar compounds. One preferred wax compound is PAROWAX®, available from Conros Corp. of Scarborough, Ontario, Canada. Waterproofing agents can be incorporated into the composition in dry form, at about 5 to 12% by weight of the total composition.

It is also desirable to include within the composition taste altering compounds that render the composition unpalatable to animals, such as humans and pets. Exemplary compositions include those having a bitter taste. One such compound is commercially available as BITREX® from McFarlane Smith Ltd. of Edinburgh, Scotland. These compounds typically are added at a very low concentration. For example, a 0.1% BITREX solution can be added to the composition at about 1 to 2% by weight of the total composition.

Useful pH-affecting additives include calcium carbonate, potassium carbonate, potassium hydroxide, ascorbic acid, tartaric acid, and citric acid. Such additives may be used at a concentration in the range of about 0.2 to 5.0% by wt., and they should be effective to adjust the pH to within a range of about 5 to 9.

The molar ratio of the metal in the metal compound to the activity promoting additive may vary between very wide ranges. By way of guidance only, it is believed that said molar ratio may usefully be in the range of about 1:0.02 to 1:58. More preferably, said molar ratio may, in certain embodiments, suitably be in the range of 1:0.3 to 1:12. Further, the metal in the simple metal compound may suitably be present at a concentration range of about 200 to 20,000 ppm (0.02 to 2.0% by weight of the composition) while the activity promoting additive may suitably be present at a concentration in the range of about 2,000 to 80,000 ppm (0.2 to 8.0% by weight of the composition). An exemplary concentration range in certain embodiments is about 0.1 to 1% by wt. of the composition for the metal and about 0.8 to 8.0% by wt. for the $Ca_2EDDS$ component.

The composition may include, but is not limited to, the presence of the following molluscicides: iron phosphate, iron EDTA, iron HEDTA, iron EDDS, metaldehyde, methiocarb, carbaryl, isolan, mexcarbate, niclosamide, trifenmorph, carbofuran, anarcardic acid, and plant-derived saponins. Such compounds may be added to the composition at a concentration in the range of about 0.01 to 5.0%, preferably about 0.2 to 5.0% by wt.

In yet another embodiment the composition may also include a fertilizer, such as virtually any plant fertilizer. Suitable fertilizers typically are granular and an example of one useful fertilizer is Ironite®, available from Ironite Products Company of Scottsdale, Ariz. When present, fertilizers may be used at a concentration in the range of about 0.5 to 10.0% by weight of the composition.

The composition of the invention typically is used in dry form and many of the constituent ingredients of the composition are included in dry form. However, it is often useful to include a sufficient amount of water within the composition to form a dough so that the ingredients can be more easily blended. Water is typically added at a concentration of about 15 to 60% by weight of the total composition. Water, however, typically is driven off by heating and drying the molluscicidal bait before it is used.

As noted above, the composition of the present invention is typically used in a dry, spreadable form such as powders, granules, cubes, or pellets. The composition may be spread on or around areas infested by molluscs as well as in areas in which mollusc infestation is to be prevented. When used to combat aquatic molluscs the composition can simply be added to the environment inhabited by the molluscs.

To prepare the composition, a suitable amount of the molluscicide and/or metal compound and the activity promoting additive can be blended in dry form, with a dry carrier material. Thereafter, other dry ingredients (such as phagostimulants and waterproofing agents) are blended and mixed with the bait. Next, suitable amounts of liquid additives (such as preservatives, taste altering additives and water) are added to the dry mixture to form a dough. The bait can be covered, such as with a plastic wrap, and heated. One preferred heating technique is by heating in a microwave oven for 30 seconds to 10 minutes. After heating, the dough can be processed in a food grinder to obtain strands of the molluscicidal composition. This material is then dried, at elevated or ambient temperatures, and it can be made into a desired form, such as powder, pellets or granules.

One exemplary molluscicidal composition can be prepared as follows. First, a mollusicidal compound, for example iron phosphate, is dry blended into cereal flour (wheat) at between 1000 to 20,000 ppm metal wt/wt. Dry $Ca_2EDDS$, is then added to the flour on a molar level to the amount of iron added. This level can vary in the range of a metal: $Ca_2EDDS$ molar ratio in the range of about 1:0.02 to 1:58 ratio. The $Ca_2EDDS$ is added to the mixture while continually stirring. Other ingredients can be added to the mixture, such as, anti-microbials (Legend), waterproofing agents, and phagostimulants (e.g., sugar). Water soluble additives are dissolved in water and then the water is blended into the dry wheat/iron compounds plus $Ca_2EDDS$ mixture. The dough is thoroughly mixed in a grinding device and extruded in the form of noodles. The resultant bait is dried at 40 degrees Celsius for 24 hours before testing.

Another exemplary molluscicidal composition can be prepared as follows.
 a) using an appropriate machine for mixing dry powders, blend the flour, sugar and mollusicide e.g. ferric sodium ethylenediamine tetraacetic acid thoroughly;
 b) add a vegetable oil to the powders and homogenize;
 c) add sufficient water (~30 kg per 1000 kg dry material), with constant mixing, to produce a damp mixture;

d) feed the mixture into a pellet mill capable of producing granules approximately 2.0-3.2 mm in diameter (5/64-1/8 in.) and 3-6 mm long (1/8-1/4 in.); and
e) if necessary, dry the resulting granules at no more than 60° C. for up to a few hours. Final moisture content should be similar to that of the starting dry materials, approximately 10-14%.

The composition may also be formulated as a liquid, especially where the composition utilizes a molluscicidal metal complex of EDDS plus $Ca_2EDDS$. In this embodiment, the $Ca_2EDDS$ could be added to an aqueous solution of ferric EDDS at a pH of about 10. By way of example, the composition added to the aquatic environment can be a concentrated formulation, with each of the metal complex of EDDs and $Ca_2EDDS$ components being present at a concentration in the range of about 2-6% by weight of applied composition.

Further aspects of the invention, including methods and uses, are set forth in the accompanying claims.

The following non-limiting examples serve to further illustrate the present invention.

Preparation of Dicalcium EDDS
Liquid Phase 100.0 g of Enviomet C265 (ethylene diamine disuccinic acid, 65% active, 0.2 moles was slurried in 1 liter of de-ionised water and $Ca(OH)_2$ (32.58 g) was added. The mixture was stirred for 17 hours before being filtered. The solution was concentrated and the product was allowed to crystallise out. The white crystalline product was collected by filtration and dried in vacuum oven at 40° C. overnight. The EDDS content was determined by HPLC to be 723.1 g, and the calcium content was determined by ICP to be 199 g. Accordingly there were two moles of $Ca^{2+}$ to one mole of EDDS anion and the compound formed is believed to be the salt, $Ca_2EDDS$.

Solid Phase 75.0 g of Enviomet C265 (ethylene diamine disuccinic acid, 65% active) was blended with 25 g of $CaCO_3$. The admixture was stored for 24 hours at room temperature before added to other components of the composition.

Example 1

Three cage tests (SCHN 08/23, SCHN 08/24, SCHN 08/30) were set up in the field. The cages with an area of 1 m² were filled with 100 l of potting soil. The surface was levelled and slightly pressed to provide an even surface, and two cabbage plants, each with five true leaves were planted in each cage. The plants were irrigated as needed. Two wooden boards (30×12.5 cm) were put in each cage as shelter for the slugs. Baits of the type noted in the table below were made the day prior to use.

|    | Iron-III-phosphate | Other ingredients | |
|----|--------------------|-------------------|---|
| A1 | 1.0% | 3.5% Enviomet ™ C265 EDDS Acid | 2.5% sugar and balance of wheat flour |
| A2 | 1.0% | 3.5% $Ca_2EDDS$ | 2.5% sugar and balance of wheat flour |

Slugs were collected from the field and 10 *Arion lusitanicus* were added to each cage at the same time as 5 g of bait. The tubs were kept in a tunnel covered with shading material to avoid direct sunlight during the assessment period.

Data was collected at 4 and 8 days after the start of the bioassays. The mortality was calculated at the end of the trial. The results obtained are shown below in Tables 1, 2 and 3.

Results of SCHN 08/23

TABLE 1

Dead slugs at 4, 8 DAT* and mortality at 8 DAT.

|         |                               | 4 DAT | 8 DAT | Mortality (%) |
|---------|-------------------------------|-------|-------|---------------|
| Control |                               | 0     | 0     | 0             |
| A1      | with 3.5% Enviomet ™ C265; EDDS acid | 8.7   | 9.0   | 90            |
| A2      | with 3.5% $Ca_2EDDS$          | 9.3   | 9.7   | 97            |

*DAT = days after start of the bioassay

Results of SCHN 08/24

TABLE 2

Dead slugs at 4, 8 DAT* and mortality at 8 DAT.

|         |                               | 4 DAT | 8 DAT | Mortality (%) |
|---------|-------------------------------|-------|-------|---------------|
| Control |                               | 0     | 0     | 0             |
| A1      | with 3.5% Enviomet ™ C265; EDDS acid | 2.0   | 8.3   | 83            |
| A2      | with 3.5% $Ca_2EDDS$          | 1.7   | 9.7   | 97            |

*DAT = days after start of the bioassay

Results of SCHN 08/30

TABLE 3

Dead slugs at 4, 8 DAT* and mortality at 8 DAT.

|         |                               | 4 DAT | 8 DAT | Mortality (%) |
|---------|-------------------------------|-------|-------|---------------|
| Control |                               | 0     | 0     | 0             |
| A1      | with 3.5% Enviomet ™ C265; EDDS acid | 5.7   | 8.7   | 87            |
| A2      | with 3.5% $Ca_2EDDS$          | 8.3   | 9.3   | 93            |

*DAT = days after start of the bioassay

Example 2

A tub test (coded POMA 09/01) was set up with 5 replicates per treatment of 5 Golden Apple Snails (GAS), *Pomacea canaliculata*. The tubs were filled with 1000 ml of tap water and stored at 22° C. The snails were added to the tubs with 2 g of bait.

Baits of the type noted in the table below were made the day prior to use.

|             | Iron-III-phosphate | Other ingredients | |
|-------------|--------------------|-------------------|---|
| A3 (Control) | —                 | —                 | Bait without active, 2.5% sugar and balance of wheat flour |
| A4          | 3.0%              | 6.0% Octaquest A65; EDDS acid | 2.5% sugar and balance of wheat flour |
| A5          | 3.0%              |                   | 2.5% sugar and balance of wheat flour |

The containers were closed with a lid with small holes for ventilation and placed on greenhouse benches in a full randomized design. After two days, with the baits remaining in the tubs, the remaining water was replaced with 1000 ml fresh tap water, and at the same time a lettuce leaf disk (Ø=7.5 cm)

was added to each tub. The bait that wasn't consumed by the snails was weighed and the bait consumption per snail was calculated.

The dead Golden Apple Snails were counted 2, 6 and 9 days after the treatment. The mortality was calculated at the end of the trial, and the results obtained are shown below in Table 4.

Results of POMA 09/01

TABLE 4

Dead Golden Apple Snails at 4, 8 DAT* and mortality at 8 DAT.

|  |  | days after treatment | | | Mortality |
|---|---|---|---|---|---|
|  |  | 2 | 6 | 9 | (%) |
| A3 Control |  | 0 | 0 | 0 | 0 |
| A4 | with 6% Enviomet ™ C265; EDDS acid | 0.0 | 0.2 | 0.4 | 8 |
| A5 | with 4.7% Ca$_2$EDDS | 0.0 | 4.6 | 4.6 | 92 |

*DAT = Days After Treatment

TABLE 5

Bait Consumption

|  |  | Bait consumption mg/snail |
|---|---|---|
| A4 | with 6.0% Enviomet ™ C265; EDDS acid | 115.2 |
| A5 | with 4.7% Ca$_2$EDDS | 202.8 |

Example 3

A tub test (coded POMA 09/05) was set up with 5 replicates per treatment of 5 Golden Apple Snails (GAS), *Pomacea canaliculata*. The tubs were filled with 1000 ml of tap water and stored at 22° C. The snails were added to the tubs with 2 g of bait.

Baits of the type noted in the table below were made the day prior to use.

|  | Iron-III-phosphate | Other ingredients | |
|---|---|---|---|
| A3 (Control) | — | — | Bait without active, 2.5% sugar and balance of wheat flour |
| A4 | 1.0% | 3.5% Enviomet ™ C265; EDDS acid | 2.5% sugar and balance of wheat flour |
| A2 | 1.0% | 3.5% Ca$_2$EDDS | 2.5% sugar and balance of wheat flour |

The containers were closed with a lid with small holes for ventilation and placed on greenhouse benches in a full randomized design. After two days the water with the left baits was replaced by 1000 ml fresh tab water and at the same time a lettuce leaf disk (Ø=7.5 cm) was added to each tub.

The dead Golden Apple Snails were counted 2, 6 and 9 days after the treatment. The mortality was calculated at the end of the trial. The results obtained are shown below in Table 6.

Results of POMA 09/05

TABLE 6

Dead Golden Apple Snails at 2, 4 DAT* and mortality at 8 DAT.

|  |  | 2 DAT | 4 DAT | Mortality (%) |
|---|---|---|---|---|
| A3 | Control | 0 | 0 | 0 |
| A4 | with 3.5% Enviomet ™ C265; EDDS acid | 1.2 | 2.0 | 40 |
| A2 | with 3.5% Ca$_2$EDDS | 2.6 | 2.8 | 56 |

*DAT = Days After Treatment

Example 4

A container test (coded JCT2-6) was set up with 2 replicates per treatment of 5 Golden Apple Snails (GAS), *Pomacea canaliculata*. The containers were filled with 600 ml of tap water and stored at 23-24° C. The snails were added to the containers with 2 g of bait.

Baits of the type noted in the table below were made prior to use.

| Code | Iron-III-phosphate | Other ingredients | |
|---|---|---|---|
| A6 | 3.0% | 6.0% Enviomet ™ C265 EDDS acid | 2.5% sugar, and balance of wheat flour |
| A7 | 3.0% | 5.8% Ca$_2$EDDS | 2.5% sugar, and balance of wheat flour |

The containers were closed with a lid with mesh for ventilation and placed in a heated wooden box in a completely randomized design. After two days, the baits remaining in the containers were removed, the remaining water was replaced with 600 ml fresh tap water and two lettuce leaf disks (diameter=5.0 cm) were added to each container. The water and the lettuce leaf discs were replaced at each of the subsequent assessments.

The dead Golden Apple snails were counted 2, 4 and 6 days after treatment and mean % mortality was calculated. The results obtained are shown below in Table 7.

Results of JC2-6

TABLE 7

Mean % Mortality of Golden Apple Snails at 2, 4 and 6 DAT*.

|  |  | days after treatment | | |
|---|---|---|---|---|
|  |  | 2 | 4 | 6 |
| Control |  | 0.0 | 0.0 | 0.0 |
| A6 | with 6% Enviomet ™ C265; EDDS acid | 10.0 | 50.0 | 50.0 |
| A7 | with 5.8% Ca$_2$EDDS | 20.0 | 70.0 | 70.0 |

*DAT = Days After Treatment

Example 5

A tub test (coded POMA 09/03a) was set up with 5 replicates per treatment of 5 Golden Apple Snails (GAS), *Pomacea canaliculata*. The tubs were filled with 1000 ml of tap water and stored at 22° C. The snails were added to the tubs with 2 g of bait. Baits of the type noted in the table below were made the day prior to use.

| | Iron-III-Phosphate | Other ingredients | |
|---|---|---|---|
| A3 (Control) | — | — | Bait without active, 2.5% sugar and balance of wheat flour |
| A6 | 3.0% | 6.0% Enviomet ™ C265; EDDS acid | 2.5% sugar, and balance of wheat flour |
| A8 | 3.0% | 8.0% admixture (75% Enviomet ™ C265 and 25% CaCO₃) | 2.5% sugar, and balance of wheat flour |

The containers were closed with a lid with mesh for ventilation and placed in a heated wooden box in a completely randomized design. After two days, the baits remaining in the containers were removed, the remaining water was replaced with 600 ml fresh tap water and two lettuce leaf disks (diameter=5.0 cm) were added to each container. The water and the lettuce leaf discs were replaced at each of the subsequent assessments.

The dead Golden Apple snails were counted 2, 6 and 9 days after treatment and mean % mortality was calculated. The results obtained are shown below in Table 8.
Results of POMA 09/03a

TABLE 8

Dead Golden Apple Snail at 2, 6, 9 DAT* and mortality at 9 DAT.

| | | days after treatment | | | Mortality |
|---|---|---|---|---|---|
| | | 2 | 6 | 9 | (%) |
| A3 Control | | 0 | 0 | 0 | 0 |
| A6 | with 6% Enviomet ™ C265; EDDS acid | 2.2 | 0.6 | 1.0 | 12 |
| A8 | with 8.0% Admixture | 2.0 | 3.0 | 3.2 | 60 |

*DAT = Days After Treatment

Example 6

A tub test (coded POMA 09/03b) was set up with 5 replicates per treatment of 5 Golden Apple Snails (GAS), *Pomacea canaliculata*. The tubs were filled with 1000 ml of tap water and stored at 22° C. The snails were added to the tubs with 2 g of bait. Baits of the type noted in the table below were made the day prior to use.

| | Iron-III-Phosphate | Other ingredients | |
|---|---|---|---|
| A3 (Control) | — | — | Bait without active, 2.5% sugar and balance of wheat flour |
| A6 | 3.0% | 6.0% Enviomet ™ C265; EDDS acid | 2.5% sugar, and balance of wheat flour |
| A8 | 3.0% | 8.0% admixture (75% Enviomet ™ C265 and 25% CaCO₃) | 2.5% sugar, and balance of wheat flour |

The containers were closed with a lid with mesh for ventilation and placed in a heated wooden box in a completely randomized design. After two days, the baits remaining in the containers were removed, the remaining water was replaced with 600 ml fresh tap water and two lettuce leaf disks (diameter=5.0 cm) were added to each container. The water and the lettuce leaf discs were replaced at each of the subsequent assessments.

The feeding on the lettuce leaves was assessed 6 and 9 days after treatment and mean % feeding reduction was calculated dead. The results obtained are shown below in Table 9.
Results of POMA 09/03b

TABLE 9

Feeding at 6, 9 DAT* and % feeding reduction at 9 DAT.

| | | days after treatment | | Feeding |
|---|---|---|---|---|
| | | 6 | 9 | reduction (%) |
| A3 Control | | 100 | 200 | 0 |
| A6 | with 6% Enviomet ™ C265; EDDS acid | 36 | 134 | 33 |
| A8 | with 8.0% Admixture | 0.0 | 64 | 68 |

*DAT = Days After Treatment

Having described the preferred embodiments of the invention, it will be apparent to one of ordinary skill in the art that other embodiments incorporating their concepts may be used. It is believed, therefore, that these embodiments should not be limited to disclosed embodiments but rather should be limited only by the spirit and scope of the appended claims. All publications and references cited herein are expressly incorporated herein by reference in their entirety. Unless otherwise noted, all percentages by weight are percent of the total composition.

The invention claimed is:

1. A molluscicidal composition, comprising:
   a molluscicide;
   a molluscicidal activity promoting additive comprising calcium ions and ethylenediamine disuccinic moieties, wherein the activity promoting additive has at least 0.6 mole of calcium per mole of ethylenediamine disuccinic moieties; and
   a carrier material edible to molluscs.

2. The composition of claim 1, wherein the activity promoting additive has at least 1 mole of calcium ions per mole of ethylenediamine disuccinic moieties.

3. The composition of claim 1, wherein the activity promoting additive has at least 1.5 mole of calcium ions per mole of ethylenediamine disuccinic moieties.

4. The composition of claim 1, wherein calcium ions are the only alkaline earth metal ions in the activity promoting additive.

5. The composition of claim 1, wherein the activity promoting additive comprises an admixture of a calcium compound and ethylenediamine disuccinic moieties.

6. The composition of claim 5, wherein the calcium compound is selected from calcium hydroxide and calcium carbonate.

7. The composition of claim 1, wherein the activity promoting additive is an admixture of a calcium compound and ethylenediamine disuccinic acid.

8. The composition of claim 7, wherein the calcium compound is selected from calcium hydroxide and calcium carbonate.

9. The composition of claim 1, further comprising a metal compound selected from the group consisting of iron, copper, zinc aluminum and mixtures thereof.

10. The composition of claim 1, wherein the molluscicide is selected from the group consisting of iron phosphate, iron chelates selected from the group consisting of iron EDTA, iron EDDS, iron polyphosphonate, iron HEDTA, iron IDA, and iron DTPA, metaldehyde, methiocarb, carbaryl, isolan, mexcarbate, mercaptodimethur, niclosamide, trifenmorph, carbofuran, anarcardic acid, plant-derived saponins, and mixtures thereof.

11. The composition of claim 1, further comprising a chelator selected from the group consisting of EDDS, EDTA, HEDTA, DTPA, IDA, HEDP, MGDA, GLDA, and derivatives thereof, and mixtures thereof.

12. The composition of claim 1, further comprising a pH-adjusting agent.

13. The composition of claim 12, wherein the pH-adjusting agent is selected from the group consisting of calcium carbonate, potassium carbonate, potassium hydroxide, ascorbic acid, tartaric acid, and citric acid.

14. The composition of claim 12, wherein the pH is in the range of about 5 to 9.

15. The composition of claim 9, wherein the molar ratio of a metal in the metal compound to the activity promoting additive is in the range of about 1:0.02 to 1:58.

16. The composition of claim 9, wherein the metal from the metal compound is present at a concentration in the composition in the range of about 200 to 20,000 ppm.

17. The composition of claim 1, wherein the activity promoting additive is present at a concentration in the range of about 0.2 to 6.0 percent by wt. of the composition.

18. The composition of claim 1, wherein the carrier is a mollusc food selected from the group consisting of wheat flour, wheat cereal, meadowfoam, agar, gelatin, oil cake, pet food wheat, soya, oats, corn, citrus mash, rice, fruits, fish by-products, sugars, coated vegetable seeds, coated cereal seeds, casein, blood meal, bone meal, yeast, fats, beer products, and mixtures thereof.

19. The composition of claim 18, wherein the mollusc food is a bone meal wheat flour mixture having a ratio of bone meal to wheat flour in the range of 50:50 to 90:10.

20. The composition of claim 9, wherein the simple metal compound is selected from the group consisting of reduced elemental iron, iron proteins, iron salts, iron carbohydrates, copper proteins, copper salts, copper carbohydrates, zinc proteins, zinc salts, zinc carbohydrates, aluminum proteins, aluminum salts, aluminum carbohydrates, and mixtures thereof.

21. The composition of claim 9, wherein the simple metal compound is selected from the group consisting of iron acetate, iron chloride, iron phosphate, iron phosphate/sodium citrate mixture, sodium iron phosphate, iron pyrophosphate, iron nitrate, iron ammonium sulfate, iron albuminate, iron sulfate, iron sulfide, iron choline citrate, iron glycerol phosphate, iron citrate, iron ammonium citrate, iron fumarate, iron gluconate, iron lactate, iron saccharate, iron fructate, iron dextrate, iron succinate, iron tartrate, copper acetate, copper chloride, copper phosphate, copper pyrophosphate, copper nitrate, copper ammonium sulfate, copper albuminate, copper sulfate, copper gluconate, copper lactate, copper saccharate, copper fructate, copper dextrate, zinc acetate, zinc chloride, zinc phosphate, zinc pyrophosphate, zinc nitrate, zinc ammonium sulfate, zinc albuminate, zinc sulfate, zinc gluconate, zinc lactate, zinc saccharate, zinc fructate, zinc dextrate, aluminum acetate, aluminum chloride, aluminum phosphate, aluminum pyrophosphate, aluminum nitrate, aluminum ammonium sulfate, aluminum albuminate, aluminum sulfate, aluminum gluconate, aluminum lactate, aluminum saccharate, aluminum fructate, and aluminum dextrate.

22. The composition according to claim 1, wherein the molluscicidal compound is selected from the group consisting of ferric ethylene diamine disuccinic acid, ferrous ethylene diamine disuccinic acid, copper ethylene diamine disuccinic acid, zinc ethylene diamine disuccinic acid, aluminum ethylene diamine disuccinic acid, and mixtures thereof.

23. The composition of claim 22, wherein the carrier material is a mollusc food.

24. The composition of claim 22, further comprising a co-active molluscicidal agent.

25. The composition of claim 24, wherein the co-active molluscicidal agent is selected from the group consisting of iron phosphate, iron EDTA, iron HEDTA, iron polyphosphonate, metaldehyde, methiocarb, carbaryl, isolan, mexcarbate, mercaptodimethur, niclosamide, trifenmorph, carbofuran, anarcardic acid, plant-derived saponins, and mixtures thereof.

26. The molluscicidal composition according to claim 1, wherein the molluscicidal activity promoting additive comprises an admixture of a calcium compound and ethylenediamine disuccinic moieties, wherein the calcium compound is selected from calcium hydroxide and calcium carbonate.

27. The composition of claim 1, wherein the activity promoting additive has at least 0.7 mole of calcium per mole of ethylenediamine disuccinic moieties.

28. A method of controlling molluscs, comprising:
applying a composition to control molluscs, the composition comprising:
a molluscicide;
a molluscicidal activity promoting additive comprising calcium ions and ethylenediamine disuccinic moieties, wherein the activity promoting additive has at least 0.6 mole of calcium per mole of ethylenediamine disuccinic moieties; and
a carrier material edible to molluscs.

29. The method of claim 28, wherein the molluscs are aquatic molluscs.

30. The method of claim 28, wherein the activity promoting additive has at least 1 mole of calcium ions per mole of ethylenediamine disuccinic moieties.

31. The method of claim 28, wherein the activity promoting additive has at least 1.5 mole of calcium ions per mole of ethylenediamine disuccinic moieties.

32. The method of claim 28, wherein calcium ions are the only alkaline earth metal ions in the activity promoting additive.

33. The method of claim 28, wherein the activity promoting additive comprises an admixture of a calcium compound and ethylenediamine disuccinic moieties.

34. The method of claim 28, wherein the activity promoting additive comprises an admixture of a calcium compound and ethylenediamine disuccinic acid.

35. The method of claim 34, wherein the calcium compound is selected from calcium hydroxide and calcium carbonate.

36. The method of claim 28, further comprising a metal compound selected from the group consisting of iron, copper, zinc aluminum and mixtures thereof.

37. The method of claim 36, wherein the molar ratio of a metal in the metal compound to the activity promoting additive is in the range of about 1:0.02 to 1:58.

38. The method of claim 36, wherein the metal is present (from the metal compound) at a concentration in the composition in the range of about 200 to 20,000 ppm.

39. The method of claim 36, wherein the metal compound is selected from the group consisting of reduced elemental iron, iron proteins, iron salts, iron carbohydrates, copper proteins, copper salts, copper carbohydrates, zinc proteins, zinc salts, zinc carbohydrates, aluminum proteins, aluminum salts, aluminum carbohydrates, and mixtures thereof.

40. The method of claim 36, wherein the metal compound is selected from the group consisting of iron acetate, iron chloride, iron phosphate, iron phosphate/sodium citrate mixture, sodium iron phosphate, iron pyrophosphate, iron nitrate, iron ammonium sulfate, iron albuminate, iron sulfate, iron sulfide, iron choline citrate, iron glycerol phosphate, iron citrate, iron ammonium citrate, iron fumarate, iron gluconate, iron lactate, iron saccharate, iron fructate, iron dextrate, iron succinate, iron tartrate, copper acetate, copper chloride, copper phosphate, copper pyrophosphate, copper nitrate, copper ammonium sulfate, copper albuminate, copper sulfate, copper gluconate, copper lactate, copper saccharate, copper fructate, copper dextrate, zinc acetate, zinc chloride, zinc phosphate, zinc pyrophosphate, zinc nitrate, zinc ammonium sulfate, zinc albuminate, zinc sulfate, zinc gluconate, zinc lactate, zinc saccharate, zinc fructate, zinc dextrate, aluminum acetate, aluminum chloride, aluminum phosphate, aluminum pyrophosphate, aluminum nitrate, aluminum ammonium sulfate, aluminum albuminate, aluminum sulphate, aluminum gluconate, aluminum lactate, aluminum saccharate, aluminum fructate, and aluminum dextrate.

41. The method of claim 28, wherein the molluscicide is selected from the group consisting of iron phosphate, iron chelates, preferably selected from iron EDTA, iron EDDS, iron polyphosphonate, iron HEDTA, iron IDA, iron DTPA; metaldehyde, methiocarb, carbaryl, isolan, mexcarbate, mercaptodimethur, niclosamide, trifenmorph, carbofuran, anarcardic acid, plant-derived saponins, and mixtures thereof.

42. The method of claim 41, further comprising a chelator selected from the group consisting of EDDS, EDTA, HEDTA, DTPA, IDA, HEDP, MGDA, GLDA, and derivatives thereof, and mixtures thereof.

43. The method of claim 28, further comprising a pH-adjusting agent.

44. The method of claim 43, wherein the pH-adjusting agent is selected from the group consisting of calcium carbonate, potassium carbonate, potassium hydroxide, ascorbic acid, tartaric acid, and citric acid.

45. The method of claim 28, wherein the pH is in the range of about 5 to 9.

46. The method of claim 28, wherein the activity promoting additive is present at a concentration in the range of about 0.2 to 6.0 percent by wt. of the composition.

47. The method of claim 28, wherein the carrier is a mollusc food.

48. The method of claim 47, wherein the mollusc food is selected from the group consisting of wheat flour, wheat cereal, meadowfoam, agar, gelatine, oil cake, pet food wheat, soya, oats, corn, citrus mash, rice, fruits, fish by-products, sugars, coated vegetable seeds, coated cereal seeds, casein, blood meal, bone meal, yeast, fats, beer products, and mixtures thereof.

49. The method of claim 47, wherein the mollusc food is a bone meal-wheat flour mixture having a ratio of bone meal to wheat flour in the range of 50:50 to 90:10.

50. The method of claim 28, wherein the composition further comprises a fertilizer material.

51. The method of claim 28, wherein:
the molluscicidal compound is selected from the group consisting of ferric ethylene diamine disuccinic acid, ferrous ethylene diamine disuccinic acid, copper ethylene diamine disuccinic acid, zinc ethylene diamine disuccinic acid, aluminum ethylene diamine disuccinic acid, and mixtures thereof.

52. The method of claim 51, wherein the carrier material is a mollusk food.

53. The method of claim 51, further comprising a co-active molluscicidal agent.

54. The method of claim 53, wherein the co-active molluscicidal agent is selected from the group consisting of iron phosphate, iron EDTA, iron HEDTA, iron polyphosphonate, metaldehyde, methiocarb, carbaryl, isolan, mexcarbate, mercaptodimethur, niclosamide, trifenmorph, carbofuran, anarcardic acid, plant-derived saponins, and mixtures thereof.

* * * * *